United States Patent [19]

Clifford et al.

[11] 4,205,551
[45] Jun. 3, 1980

[54] SEAL TESTER

[75] Inventors: Earl W. Clifford, Getzville; August Scherer, Tonawanda, both of N.Y.

[73] Assignee: The Aro Corporation, Bryan, Ohio

[21] Appl. No.: 26,180

[22] Filed: Apr. 2, 1979

[51] Int. Cl.² .................................................. G01M 3/28
[52] U.S. Cl. ........................................ 73/52; 73/49.2; 73/49.3
[58] Field of Search ............... 73/52, 49.3, 49.2, 40.7, 73/40, 37

[56] References Cited

U.S. PATENT DOCUMENTS

| 900,324 | 10/1908 | Swangren | 73/49.3 |
|---|---|---|---|
| 2,107,922 | 2/1938 | Westin | 73/40 X |
| 2,885,892 | 5/1959 | Coutts | 73/40 X |
| 3,251,218 | 5/1966 | Russell | 73/52 |
| 3,958,448 | 5/1976 | Willis et al. | 73/49.2 X |

*Primary Examiner*—Gerald Goldberg
*Assistant Examiner*—Joseph W. Roskos
*Attorney, Agent, or Firm*—Sommer & Sommer

[57] ABSTRACT

Apparatus is provided for testing the strength of a seal provided between an underlying substrate material and an overlying sheet material of a container. The package is inflated through an inflation needle inserted into the container. The pressure in the container is sensed through a sensing needle inserted therein. The apparatus may be used to test the tensile strength of the seal, and the location of any leaks therein.

11 Claims, 7 Drawing Figures

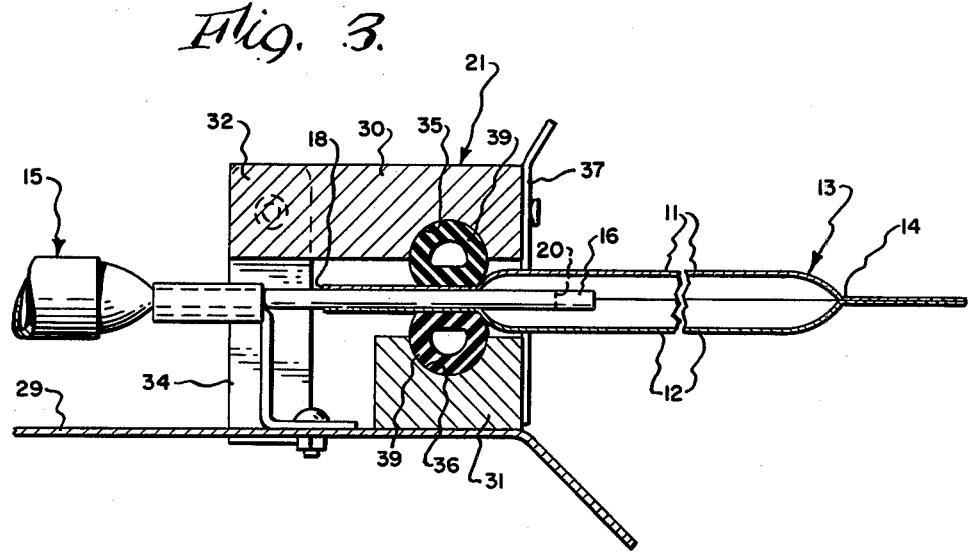
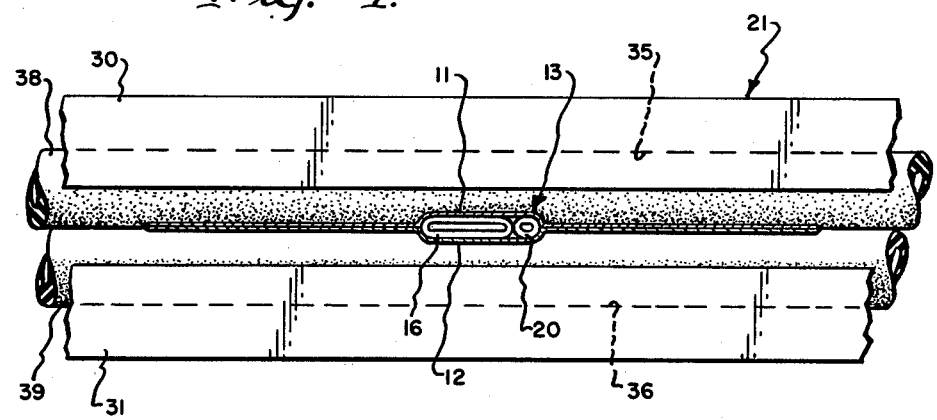
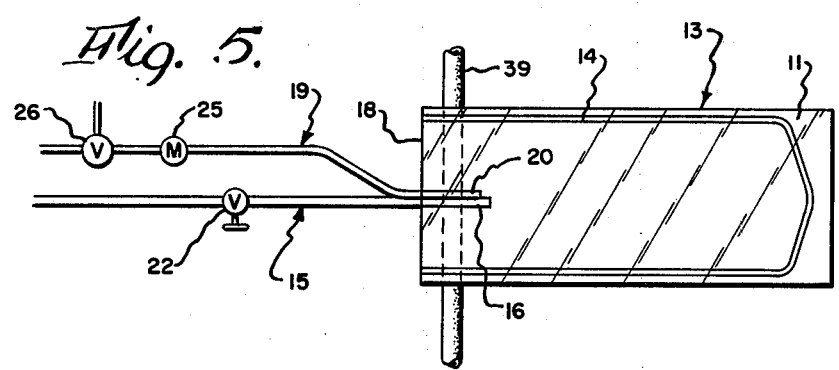

SEAL TESTER

BACKGROUND OF THE INVENTION

1. Field of the Invention

The present invention relates generally to the field of tensile strength testers, and more particularly to improved apparatus for testing the strength of a marginal seal provided between overlying and underlying materials of a container.

2. Description of the Prior Art

Containers, such as packages and pouches, have a wide variety of applications. Many of these contemplate that an overlying sheet material be sealed to an underlying or substrate material. Examples of there containers include food packages, containers for surgical instruments, parts of a general nature, and the like. The seals may be provided by a number of different techniques. For example, heat sealing and adhesive sealing are two popular techniques in widespread use.

In more recent years, it has become common to package surgical instruments in sterlized containers. These containers may be initially formed with an open unsealed side, to permit insertion of the instrument, after which opening is closed. The integrity of the seal in such medical applications is of paramount importance. In an effort to provide guides for manufacturers, standards have been developed. One such standard is a common tensile test. A portion of the package is cut out, and the sealed materials are pulled apart to determine the tensile strength of the seal. While this may have some acceptance, this test does not indicate the existence of a fault in some untested part of the seal. Accordingly, there is a need to test the strength of a seal along its entire length.

SUMMARY OF THE INVENTION

The present invention provides apparatus for testing the strength of a seal provided between an overlying and substrate material of a container. The apparatus broadly comprises: inflation means including an inflation needle or tube adapted to be inserted into the container, and operatively arranged to selectively inflate the container with a fluid; and sensing means, including a sensing tube or needle, adapted to be inserted into the container, and operatively arranged to sense the pressure of such fluid therein. The inflation and sensing members may be inserted through an open portion of the container, after which such open portion is clamped to effectively seal the container. Alternatively, the inflation and sensing members may actually penetrate the container wall. If desired, the fluid may contain a suitable dye to visually indicate the location of any leaks or imperfections.

One object of the present invention is to provide improved apparatus for testing the strength of a seal provided between two layers of a container.

Another object is to provide such apparatus which is further capable of indicating the location of a leak.

These and other objects and advantages will become apparent from the foregoing and ongoing specification, the drawings, and the appended claims.

BRIEF DESCRIPTION OF THE DRAWINGS

FIG. 3 is a fragmentary enlarged vertical sectional view thereof, taken generally on line 3—3 of FIG. 1, showing the inflation and sensing tubes inserted through the container open portions, with the cushioned bars clamped down thereon.

FIG. 4 is a fragmentary enlarged vertical sectional view thereof, taken generally on line 4—4 of FIG. 1, and principally showing the cross-sections of the inflation and sensing tubes.

FIG. 5 is a schematic view thereof, showing the inflation and sensing means.

DESCRIPTION OF THE PREFERRED EMBODIMENTS

Figure 1:
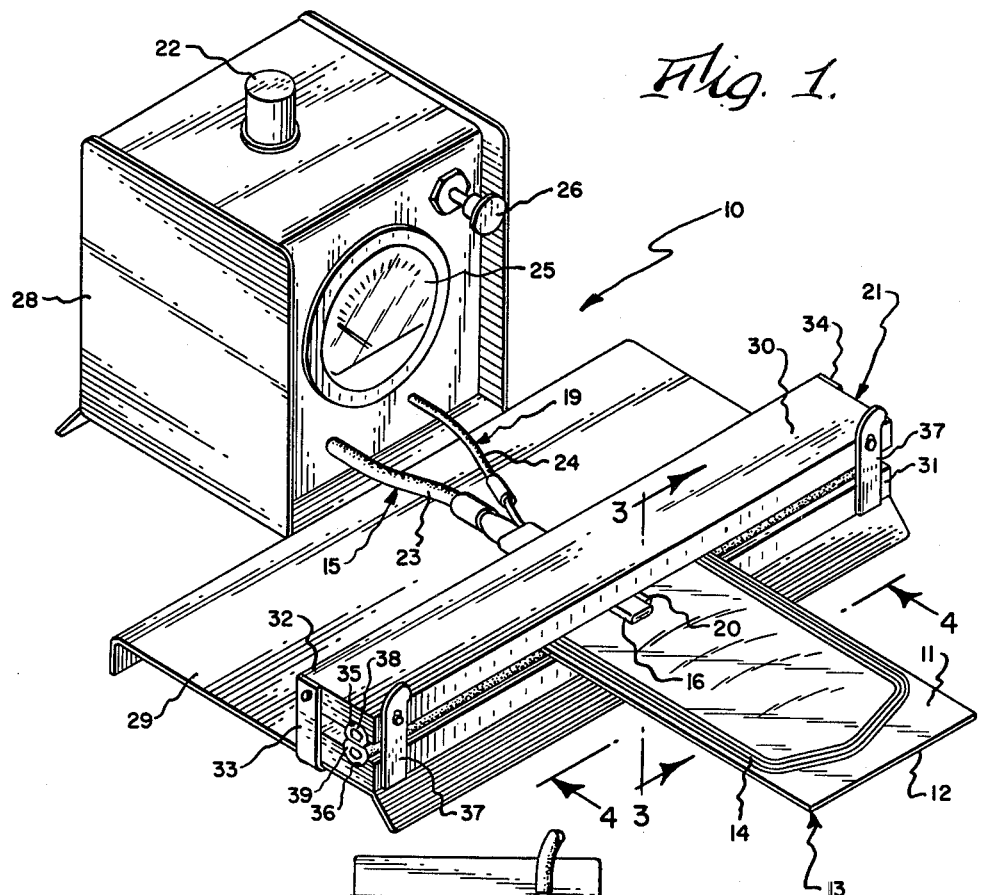
FIG. 1 is a perspective view of a first preferred embodiment of the apparatus in association with a partially-enclosed container.

At the outset, it should be clearly understood that like reference numerals are intended to identify the same elements and/or structure consistently through the several drawing figures, as such elements and/or structure may be further described or explained by the entire written specification of which this detailed description is an integral part.

Figure 6:
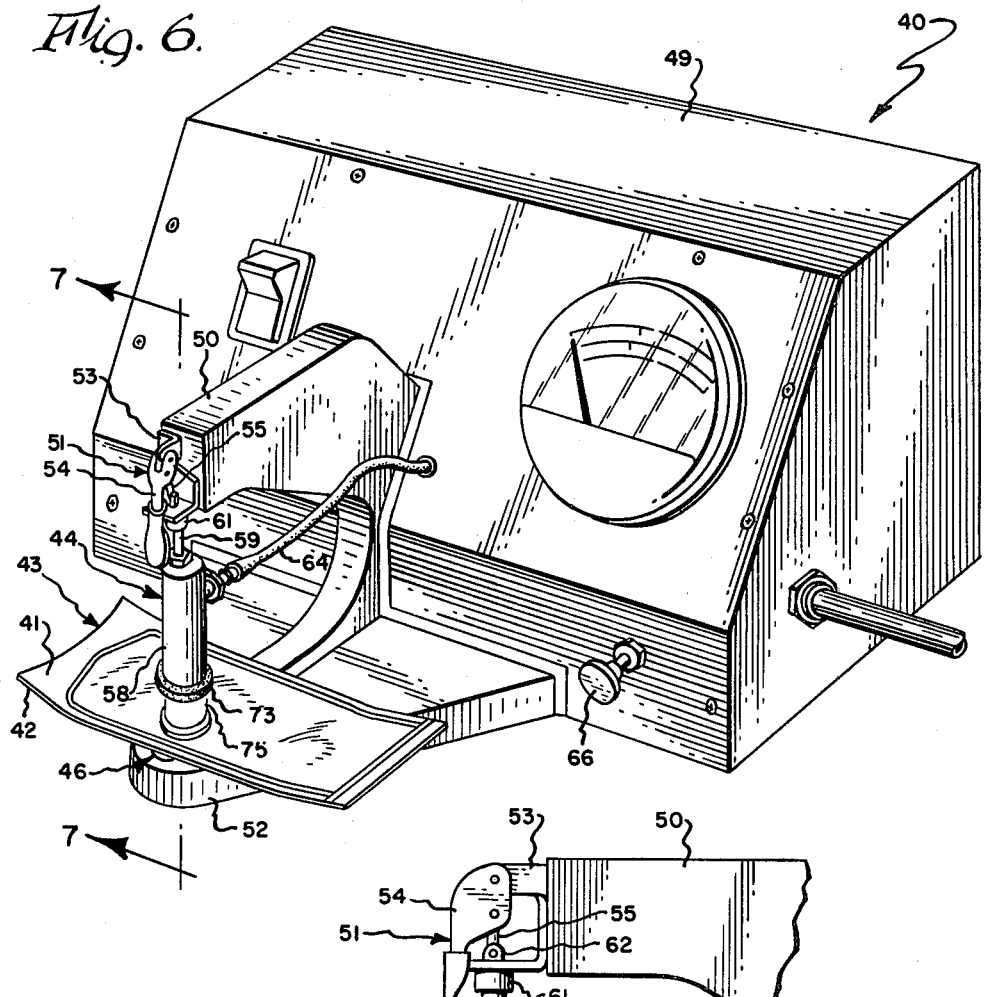
FIG. 6 is a perspective view of a second preferred embodiment of the apparatus in association with a fully-enclosed container.
Figure 7:
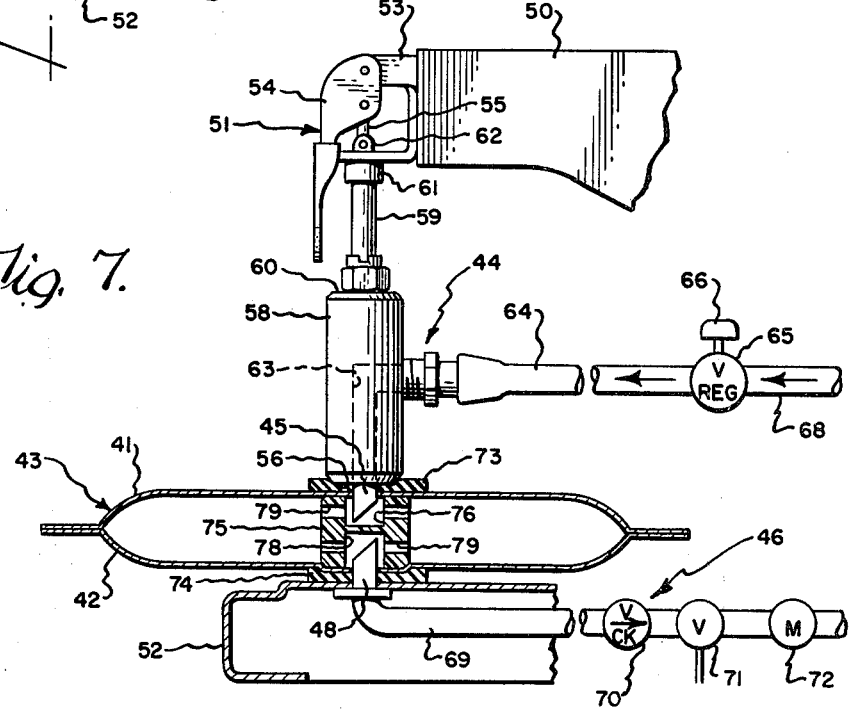
FIG. 7 is a fragmentary enlarged vertical sectional view thereof, taken generally on line 7—7 of FIG. 6, showing the inflation and sensing needles as penetrating the upper and lower container walls, respectively.

Referring to the drawings, the present invention provides improved apparatus for testing the strength of a perimetrical or marginal seal provided between a sheet material and a substrate material. The embodiment disclosed in FIGS. 1–5 is particularly adapted for use with a partially-enclosed container, in which the sheet and substrate materials are unsealed along a portion of their overlapping lengths. The embodiment illustrated in FIGS. 6 and 7 is particularly suited for use with a fully-enclosed container.

Referring now to FIGS. 1–5, and more particularly to FIG. 1 thereof, the first embodiment provides apparatus, of which the presently preferred embodiment is generally indicated at 10, which is particularly suited for use in testing the strength of a perimetrical seal provided between an upper sheet material 11 and a lower substrate material 12 of a partially-enclosed container, generally indicated at 13. The particular container depicted in FIG. 1, is of the type used to contain surgical instruments and the like. These containers or pouches are normally heat-sealed along three sides, the seals being indicated at 14, with the fourth side being normally closed and sealed after a sterilizer instrument (not shown) has been inserted into the container. In this type of container, the sheet material is normally some type of transparent plastic material, and the substrate material may be some type of treated paper. However, it should be pointed out that the improved apparatus is not limited to use with this particular type of container, but may be used with other types of bags, containers, pouches, and the like. Moreover, the particular materials of which the sheet and substrate components are composed are not deemed to be critical; nor is the manner by which the seal is provided, be it by heat and/or pressure, an adhesive, or by some other means. Likewise, the seal need not extend continuously around the entire perimetrical margin of the container, as in the case where a suitable sheet material is folded upon itself to form overlying sheet and substrate layers. Hence, the terms "container", "seal", "sheet material" and "substrate material" should be broadly construed.

In FIG. 1, the improved apparatus 10 is shown as broadly comprising: inflation means, generally indicated at 15, having an inflation tube 16 adapted to be inserted into the container through the unsealed open fourth side 18 thereof (FIG. 3), and operatively arranged to selectively inflate the container with a suitable fluid, such as compressed air; sensing means, generally indicated at 19, having a sensing tube 20 adapted to be inserted through such container open portion 18, and operatively arranged to sense the pressure of such fluid in the container; and clamping means, generally indicated at 21, adapted to releasably close the container open portion 18 when the inflation and sensing tubes are inserted into the container to sealingly close such open portion.

The inflation means 15 is suitably connected to a compressed air source (not shown), and includes a control valve 22 for regulating the fluid pressure supplied by the source, a flexible hose 23, and inflation tube 16. As best shown in FIG. 4, the inflation tube appears to have a horizontally-elongated relatively flat transverse cross-section to facilitate the sealing deformation of cushioning tubes, later described.

Figure 2:
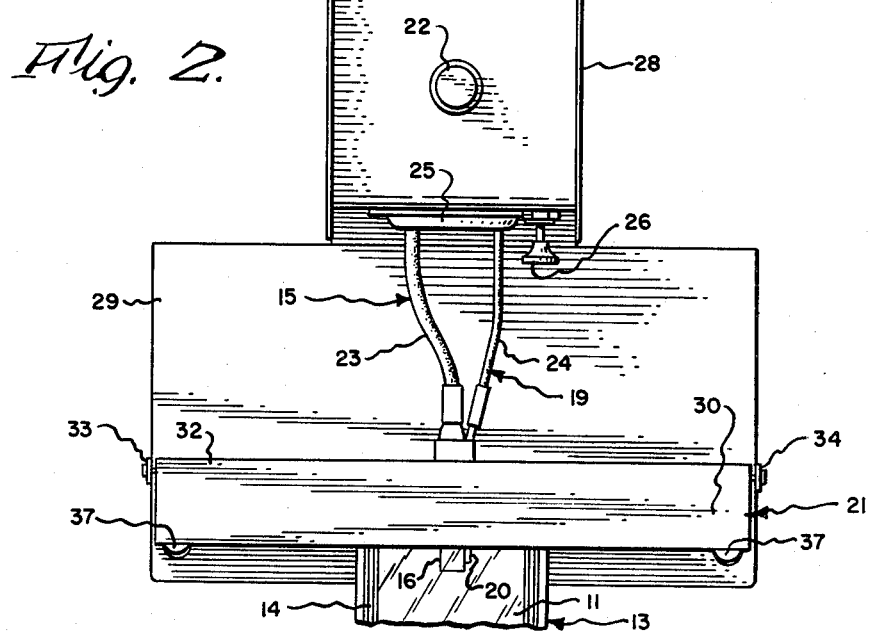
FIG. 2 is a top plain view thereof.

The sensing means 19 includes sensing tube 20, a flexible hose 24, a suitable pressure indicating meter 25, and a vent valve 26 which may be manually activated between tests to discharge and vent any pressure in the sensing means. If desired, a suitable check valve (not shown) may be placed in the sensing means so that meter 25 will indicate the pressure in the container immediately prior to rupture. In effect, use of such check valve prevents the meter 25 from falling back to zero after rupture. Hence, the meter may be reset by operation of the vent valve. In FIGS. 1 and 2, the meter, vent valve, and pressure regulating valve are all shown as being contained within a suitable cover 28.

The clamping means 21 is shown as being mounted on a rectangular table 29 which extends forwardly from the cover 28. As best shown in FIGS. 1 and 3, the clamping means includes a pair of horizontally-elongated upper and lower bars 30, 31, respectively. The lower bar 31 is mounted directly on table 29. A rearward marginal portion 32 of the upper bar 30 is pivotally mounted on a pair of left and right upstanding brackets 33, 34, which are mounted on the table. Hence, the upper bar 30 is mounted for pivotal movement toward and away from the lower bar 31. The upper and lower bars are substantially parallel to one another when the clamping means is in the closed position (FIGS. 1, 3 and 4), and may be locked in this position by leaf clamps 37.

In FIG. 3, the upper and lower bars 30, 31 are shown provided with horizontally-elongated concave recesses 35, 36, which are arranged to face one another. Elongated hollow cushioning tubes, 38, 39, each formed of a suitable resilient or deformable material, are mounted in the upper and lower bar recesses, respectively. These tubes 38, 39 are arranged to releasably close the open side 18 of the container when the clamping means is closed, and will readily deform about, and assume the contour of, the inserted inflation and sensing tubes. While the preferred embodiment is shown and described as including such cushioning tubes 38, 39, persons skilled in this are will readily appreciate that many functionally-equivalent devices may be substituted therefor to releasably close and substantially seal the container open portion or side.

If desired, the fluid supplied through the inflation tube may contain a suitable dye or discolorant. Hence, if there is a pin hole leak in the seal, the dye-containing fluid will escape through such leak and the dye will stain or indicate the exact location of such leak.

Referring now to FIGS. 6 and 7, a second preferred embodiment of such apparatus, generally indicated at 40, is adapted for use in testing the strength of a perimetrical seal provided between an upper sheet material 41 and a lower substrate material 42 of a fully-enclosed container, generally indicated at 43. The particular container depicted in FIGS. 6 and 7 is the same as the container illustrated in FIGS. 1–5, save that the fourth side thereof has been sealed. Again, this particular container is merely an illustrative specimen of the many different types of containers that may be tested with the improved apparatus.

In FIG. 6, the improved apparatus 40 is shown as broadly comprising: inflation means, generally indicated at 44, including an inflation needle 45 (FIG. 7) adapted to penetrate the container at one location, and operatively arranged to selectively inflate the container with a fluid; and sensing means generally indicated at 46, including a sensing needle 48 (FIG. 7) adapted to penetrate the container at another location and operatively arranged to sense the pressure in the container.

As best shown in FIG. 6, portions of the inflation and sensing means 44, 46 are mounted on the distal ends of a C-shaped frame which extends forwardly from an enclosing cover 49. Specifically, the inflation needle 45 is mounted on the frame's upper arm 50 through an intermediate toggle linkage, generally indicated at 51, for vertical movement toward and away from the stationary sensing needle 48, which is mounted on the frame's lower arm 52.

The toggle linkage 51 is shown as including a bracket member 53 extending forwardly from frame upper arm 50, a handle member 54 pivotally mounted on the bracket member, and a connecting link 55 having one marginal end portion pivotally mounted on the handle member at a location eccentric to the handle member's pivotal axis.

The inflation needle 45 is shown as extending downwardly beyond the lower horizontal annular end face 56 of a vertically-elongated cylindrical body 58. A rod 59 extends vertically upwardly from the body's upper horizontal end face 60. This rod has an intermediate portion passed through a guide collar 61 mounted on the toggle bracket, and has its upper marginagl end portion 62 pivotally connected to the other marginal end portion of connecting link 55. Hence, toggle handle 54 may be moved clockwise from the position shown in FIG. 7, to raise the inflation needle; thereby moving it away from the sensing needle, and vice versa. The cylindrical body 58 is provided with an L-shaped internal passageway 63 communicating the inflation needle 45 with a pressurized fluid source (not shown), such as compressed air, through a flexible hose 64, a suitable variable valve 65 controlled by rotatable knob 66, and supply pipe 68.

The sensing needle 48 extends upwardly from the frame's lower arm 52. As best shown in FIG. 7, sensing needle 48 is connected via conduit 69, check valve 70, vent valve 71, and meter 72 to exhaust. Check valve 70 is arranged to apply the pressure sensed through the sensing needle, to the meter until vent valve 71 is suitably manipulated to dump such pressure.

In the preferred embodiment, annular cushions 73, 74 surround the inflation and sensing needles 45, 48, respectively. These cushions, which are conveniently formed of a resilient material, are operatively arranged to sealingly engage the container when the inflation needle is inserted therein.

To accommodate penetration by the inflation and sensing needles, a receiver member 75 may be sealed within the container. This receiver member 75 is shown as being a vertically-elongated cylindrical member having upper and lower recesses 76, 78 extending therein from its upper and lower surfaces, respectively. These recesses communicate with the interior of the container through a plurality of ports, severally indicated at 79.

In operation, receiver member 75 is first sealed within container 43. Thereafter, the container is positioned between the needles, and toggle linkage 51 is manipulated to lower the inflation needle. The sensing needle 48 will penetrate the substrate material, and be received in receiver member lower recess 78. The inflation needle 45 will penetrate the upper sheet material, and be received in receiver member upper recess 76. In this position, cushions 73, 74 will effectively seal the openings about the inflation and sensing needles. Once the needles have been so inserted, pressurized fluid, which may contain an optional dye, may be supplied to the container through the inflation needle. At the same time, the pressure in the container may be sensed through the sensing needle and indicated on the meter 72.

While the two embodiments differ in adaptation to a partially-enclosed container (FIGS. 1-5) or to a fully-enclosed container (FIGS. 6 and 7), both embodiments may be similarly employed to determine useful emperical data on the strength of the seal. For example, the container may be sufficiently inflated to determine the pressure at which the seal fails. Or, the container may be inflated to a lesser pressure to determine that the seal has maintained its sealing integrity at such test pressure. These pressures, as read by the sensing meter, may be suitably calibrated to reflect the tensible force which urges the sheet and substrate materials to separate at the seals. If the fluid contains a dye, the operator may examine the seal for possible failure at different test pressures, the escaping dye staining or discoloring the seal about the location of such failure. Repeated leaks at the same location may suggest that a particular aspect of the sealing process needs correction, for example, caused by a bubble being propagated ahead of sealing rollers. This may suggest that pressure or temperature parameters need adjustment. Of course, the improved apparatus may be used to test many different types of seals provided between two overlapping sheets.

Therefore, while two preferred embodiments have been shown and described, and several modifications thereof discussed, persons skilled in this art will appreciate the various additional changes and modifications may be made without departing from the spirit of the invention, as defined by the following claims.

What is claimed is:

1. Apparatus for testing the strength of a seal provided between a sheet material and a substrate material of a partially-enclosed container, said sheet and substrate materials being unsealed along a portion of their overlapping lengths, said apparatus comprising:
   inflation means having an inflation tube adapted to be inserted into said container through said open portion, and arranged to selectively inflate said container with a fluid;
   sensing means having a sensing tube adapted to be inserted into said container through said open portion, and arranged to sense the pressure of such fluid in said container; and
   clamping means adapted to releasably close said container open portion when said inflation and sensing tubes are inserted into said container to sealingly close said open portion.

2. The apparatus as set forth in claim 1 wherein said clamping means includes upper and lower bar means having portions mounted for movement toward and away from one another, and cushion means carried by said bar means portions and adapted to sealingly close said container open portion about such inserted inflation and sensing tubes.

3. The apparatus as set forth in claim 2 wherein said bar means are mounted for pivotal movement relative to one another.

4. The apparatus as set forth in claim 2 wherein said cushion means includes a resilient member adapted to be deformed about said inserted inflation and sensing tubes when said bar means portions are moved toward one another.

5. The apparatus as set forth in claim 1 wherein said fluid includes a dye.

6. Apparatus for testing the strength of a seal provided between a sheet material and a substrate material of a fully-enclosed container, comprising:
   inflation means including an inflation needle adapted to penetrate said container at one location, and arranged to selectively inflate said container with a fluid; and
   sensing means including a sensing needle adapted to penetrate said container at another location and arranged to sense the pressure of such fluid in said container.

7. The apparatus as set forth in claim 6 and further comprising:
   a cushion surrounding said inflation needle and adapted to sealingly engage said container when said inflation needle is inserted therein.

8. The apparatus as set forth in claim 6 and further comprising:
   a cushion surrounding said sensing needle and adapted to sealingly engage said container when said sealing needle is inserted therein.

9. The apparatus as set forth in claim 6 wherein said inflation needle is adapted to penetrate one of said materials, and said sensing needle is adapted to penetrate the other of said materials.

10. The apparatus as set forth in claim 6 wherein one of said needles is mounted for movement toward and away from the other of said needles.

11. The apparatus as set forth in claim 6 wherein said fluid includes a dye.

* * * * *